United States Patent
Vreeman et al.

(10) Patent No.: US 8,740,841 B2
(45) Date of Patent: *Jun. 3, 2014

(54) EXTENSION TUBES FOR BALLOON CATHETERS

(75) Inventors: Daniel Vreeman, Rogers, MN (US); Jason Eddy, St. Michael, MN (US); Sandra Kallio, Circle Pines, MN (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/550,037

(22) Filed: Jul. 16, 2012

(65) Prior Publication Data

US 2012/0283767 A1 Nov. 8, 2012

Related U.S. Application Data

(63) Continuation of application No. 12/131,599, filed on Jun. 2, 2008, now Pat. No. 8,257,304.

(60) Provisional application No. 60/941,288, filed on Jun. 1, 2007.

(51) Int. Cl.
*A61M 29/00* (2006.01)

(52) U.S. Cl.
USPC .................. 604/96.01; 604/103; 606/194

(58) Field of Classification Search
USPC .................. 604/96.01, 103, 103.04, 103.09; 606/194
See application file for complete search history.

(56) References Cited

U.S. PATENT DOCUMENTS

| | | | |
|---|---|---|---|
| 4,793,351 A | 12/1988 | Landman et al. | |
| 4,951,976 A * | 8/1990 | Boelkins | 285/114 |
| 5,047,045 A | 9/1991 | Arney et al. | |
| 5,100,381 A | 3/1992 | Burns | |
| 5,209,728 A | 5/1993 | Kraus et al. | |
| 5,290,241 A | 3/1994 | Kraus et al. | |
| 5,304,134 A | 4/1994 | Kraus et al. | |
| 5,498,240 A * | 3/1996 | Bagaoisan et al. | 604/96.01 |
| 5,569,196 A | 10/1996 | Muni et al. | |
| 5,769,819 A | 6/1998 | Schwab et al. | |
| 6,129,708 A * | 10/2000 | Enger | 604/103.04 |
| 7,273,485 B2 | 9/2007 | Simpson et al. | |
| 8,012,300 B2 | 9/2011 | Simpson et al. | |
| 8,257,304 B2 * | 9/2012 | Vreeman et al. | 604/96.01 |
| 2005/0131445 A1 | 6/2005 | Holman et al. | |

OTHER PUBLICATIONS

An International Search Report corresponding to International Application No. PCT/US2008/065530, completed Sep. 17, 2008 and mailed Jul. 10, 2008; 3 pages.

* cited by examiner

*Primary Examiner* — Theodore Stigell
(74) *Attorney, Agent, or Firm* — Alana T. Bergman, Esq.

(57) ABSTRACT

A balloon catheter may include a multi-lumen tube having an inflation lumen and a guide wire lumen. The multi-lumen tube may include a proximal end and a distal end and may terminate at a distal tip. The catheter may include an extension tube extending distally from the distal tip of the multi-lumen tube and a dilatation balloon disposed about the multi-lumen tube and the extension tube. The distal tip of the multi-lumen tube may be under the balloon.

24 Claims, 3 Drawing Sheets

EXTENSION TUBES FOR BALLOON CATHETERS

CROSS-REFERENCE TO RELATED APPLICATION

This application is a continuation of U.S. patent application Ser. No. 12/131,599, filed Jun. 2, 2008, now U.S. Pat. No. 8,257,304, which claims the benefit under 35 U.S.C. §119(e) of provisional application Ser. No. 60/941,288 filed Jun. 1, 2007, the entire contents of which are incorporated herein by this reference.

FIELD OF THE INVENTION

The present disclosure relates to extension tubes for balloon catheters. More particularly, the disclosure is directed to extension tubes for catheter shafts configured to be used with dilatation balloons to treat a relatively long stenosis of blood vessels.

BACKGROUND OF THE INVENTION

Balloon catheter systems for percutaneous angioplasty are well known. The catheter can be introduced to the coronary artery through the femoral artery. A guide wire is initially positioned within the coronary artery and a dilation catheter is advanced into the coronary artery over the guide wire. Near the tip of the distal end of the dilation catheter is a deflated distensible balloon, which can be inflated with fluid. The inflated balloon can compress a stenosis towards the wall of the vessel. In another example, the catheter can be introduced over a guide wire into the femoral artery from a percutaneous access site in the contralateral femoral artery. Subsequent balloon inflation can compress a stenosis towards the wall of the vessel.

In the treatment of longer stenoses, the balloon lengths, and any associated lengths, are necessarily increased. During treatment, inflation of the balloon can cause the catheter to undesirably bow or bend, which can result in possible damage to the vessel wall. The bowing or bending of the catheter can result in permanent deformation of a pre-mounted stent associated with the catheter. Accordingly, there remains a need to develop a catheter useful for the treatment of longer arterial vessels.

SUMMARY OF THE INVENTION

In accordance with various aspects of the disclosure, a balloon catheter may include a multi-lumen tube having an inflation lumen and a guide wire lumen. The multi-lumen tube may include a proximal end and a distal end and may terminate at a distal tip. The catheter may include an extension tube extending distally from the distal tip of the multi-lumen tube and a dilatation balloon disposed about the multi-lumen tube and the extension tube. The distal tip of the multi-lumen tube may be under the balloon.

According to some aspects of the disclosure, a method for making a balloon catheter may include narrowing a portion of a multi-lumen tube such that a distal end of the multi-lumen tube has a diameter smaller than that of a remainder of the multi-lumen tube, flaring an opening to a guide wire lumen at a distal tip of the multi-lumen tube, inserting an extension tube into the flared opening of the guide wire lumen, connecting a proximal neck of a dilatation balloon to an unnarrowed portion of the multi-lumen tube, and connecting a distal neck of a dilatation balloon to the extension tube, such that the distal tip of the multi-lumen tube is under the balloon

BRIEF DESCRIPTION OF THE DRAWINGS

Various embodiments of the disclosure will be understood from the following description, the appended claims, and the accompanying drawings, in which:

DETAILED DESCRIPTION

One exemplary aspect of the present disclosure provides a balloon catheter having an extension at its distal end to treat a relatively long stenosis of arterial vessels.

Figure 1:
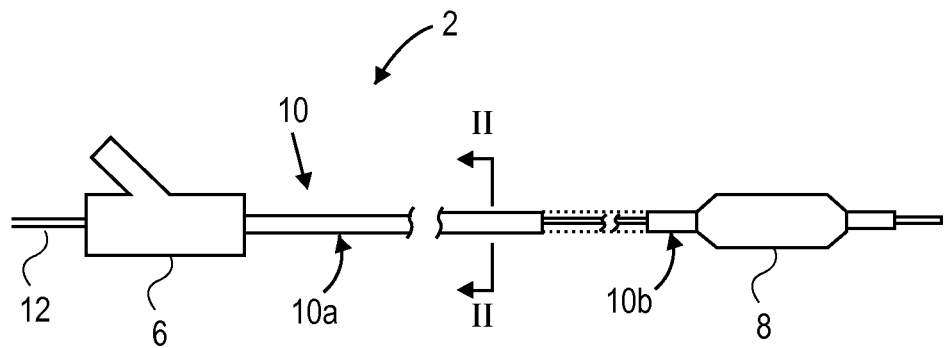
FIG. 1 is a side view of an exemplary dilatation balloon catheter in accordance with various aspects of the disclosure.

An exemplary balloon catheter is illustrated in FIG. 1. The catheter 2 may comprises a multi-lumen tube 10 having a proximal end 10a and a distal end 10b. Referring to the cross-section view of FIG. 2, the multi-lumen tube 10 may include a guide wire lumen 22 and an inflation lumen 20. The guide wire lumen 22 may be sized to receive a guide wire 12 such that the guide wire lumen 22 may be moved relative to the guide wire 12 so that the distal end 10b of the catheter 2 may be directed to the location of a stenosis of a vessel. Persons skilled in the art may refer to catheter 2 as an "over-the-wire" catheter. While the invention is described using an "over-the-wire" catheter as an example, it is recognized that the invention is equally applicable to "rapid exchange" catheters as well, where the guidewire lumen extends over only a distal portion of the catheter and is typically 5-50 cm in length.

The catheter 2 may include a manifold 6, for example, a Y-manifold, such that the manifold 6 is at the proximal end 10a of the multi-lumen tube 10 during use. The catheter 2 may include a dilatation balloon 8 at the distal end 10b of the multi-lumen tube. The inflation lumen 20 may convey fluids from a fluid source (not shown) to the dilatation balloon 8 in order to inflate the balloon 8.

Dimensions and materials for the guide wire and dilatation catheter are known in the art and are described, for example, in U.S. Pat. No. 4,545,390, the disclosure of which is incorporated herein by reference.

Where a stenosis may be relatively long, longer dilatation balloons may be necessary. However, as the length of the balloon increases, longitudinal lengthening of the balloon upon radial expansion increases proportionally. If the catheter is not lengthened in proportion to the balloon lengthening, the distal portion of the catheter can experience a curvature in the shape of a banana/crescent shape or an S-shape, which can result, for example, from a twist in the balloon during bonding to the catheter. This bowing or bending of the catheter can result in permanent deformation of a pre-mounted stent associated with the catheter.

Figure 3A:
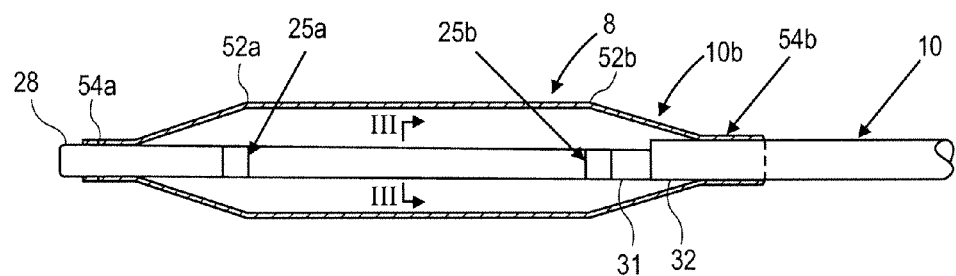
FIG. 3A is a combination plan and cross-sectional side view of the distal end of an extended length catheter with balloon in accordance with various aspects of the disclosure.

FIG. 3A is a side view of the distal end 10b of the multi-lumen tube 10, with the dilatation balloon 8 illustrated in cross-section. Referring now to FIG. 3, the balloon catheter 2 may include an extension tube 28 extending from the distal end 10b of the multi-lumen tube 10. The extension tube 28 may provide the catheter 2 with the ability to reduce or even eliminate the aforementioned balloon curvature during inflation.

The balloon 8 may include distal and proximal necks 54a, 54b at opposite ends of the balloon 8 and distal and proximal cone transition regions 52a, 52b between the necks 54a, 54b. The extension tube 28 may include distal and proximal marker bands 25a, 25b that may indicate the position of the two balloon cone transition regions 52a (distal) and 52b (proximal). According to some aspects, the distal and proximal balloon necks 54a, 54b may be coupled with the extension tube 28 and the multi-lumen tube 10, respectively.

Figure 3C:
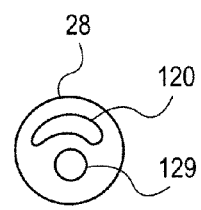
FIGS. 3B and 3C are cross-sectional views of the catheter along line of FIG. 3 illustrating two exemplary configurations of the extension tube.
Figure 3B:
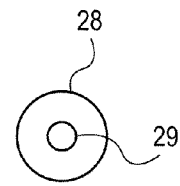

Referring to FIG. 3B, according to an exemplary embodiment, the extension tube 28 may include a guide wire lumen 29 sized to receive the guide wire 12 such that the guide wire lumen 29 may be moved relative to the guide wire 12 so that the extension tube 28 may be directed to the location of a stenosis of a vessel. The guide wire 12 may extend from the guide wire lumen 22 of the multi-lumen tube 10 through the guide wire lumen 29 of the extension tube 28 and past the balloon 8. The inflation lumen 20 may terminate at the distal end 10b of the multi-lumen 10 and within the length of the dilatation balloon 8. The inflation lumen 20 may fluidly communicate with an interior volume of the dilatation balloon 8 via one or more radial and/or longitudinal openings.

Referring to FIG. 3C, according to an exemplary embodiment, the extension tube 28 may include a guide wire lumen 129 and an inflation lumen 120. The guide wire lumen 129 may be sized to receive the guide wire 12 such that the guide wire lumen 129 may be moved relative to the guide wire 12 such that the extension tube 28 may be directed to the location of a stenosis of a vessel. The guide wire 12 may extend from the guide wire lumen 22 of the multi-lumen tube 10 through the guide wire lumen 129 of the extension tube 28 and past the balloon 8. The inflation lumen 120 may convey fluids from a fluid source (not shown), by way of the inflation lumen 20, to the dilatation balloon 8 in order to inflate the balloon 8. The inflation lumen 120 and/or the inflation lumen 20 may fluidly communicate with an interior volume of the dilatation balloon 8 via one or more radial and/or longitudinal openings.

According to some aspects of the disclosure, the multi-lumen tube 10 and the extension tube 28 may comprise the same materials or different materials. For example, according to various aspects, the tubes 10, 28 may comprise various polymers, copolymers, or blends. For example, the materials may be selected from Pebax®, nylons, etc. In some aspects, the extension tube 28 may comprise at least one nylon material that is different from that of the multi-lumen tube 10. A "different" nylon material can refer to nylons comprising at least one different monomer type. Alternatively, a different nylon material can comprise a copolymer or blend of the same monomer type, but with different respective weight ratios of the monomers. Exemplary nylons include, but are not limited to, homopolymers, copolymers, and blends made from nylon 12, nylon 11, nylon 66, etc. In various aspects, the nylon materials can include other non-nylon forming monomers, such as, for example, ether forming monomers. In some aspects, the material may comprise polyether block polyamides, such as those available commercially as Pebax®.

According to various aspects of the disclosure, the extension tube 28 may be less stiff than the multi-lumen tube 10. That is, the extension tube 28 may have a lower hardness value so as to minimize the tendency of the balloon-containing portion of the catheter from forming a banana shape. The hardness of polymeric materials is typically indicated by Shore or Durometer hardness. Hardness is determined with a gauge that measures the resistance of the polymer toward deformation, e.g., indentation or elongation. In one embodiment, the hardness of the multi-lumen and extension tubes 10, 28 are measured with the Shore D scale.

Although the extension tube 28 may have a reduced hardness value than the multi-lumen tube 10, it should not be undesirably flexible. Excessive deformation and/of elongation of the extension tube 28 may inhibit balloon rewrap due to the excessive deformed length of extension tube 28. An increased force may be required to pull the poorly rewrapped balloon back into an introducer sheath or a guide catheter.

According to some aspects of the disclosure, the Shore hardness of extension tube 28, multilumen tube 10, or both can range, for example, from 25D to 95D. In various aspects, the desired hardness of the extension tube 28 and/or multilumen tube 10 can be achieved by blending nylon materials of different hardness and/or by changing the wall thickness of the extension tube 28 and/or multilumen tube 10, respectively. For example, nylons ranging from 25D to 90D hardness may be utilized to achieve an intermediary hardness. For example, the hardness of a 65D material can be decreased by blending with a material of lower hardness. The specific hardness values can be ultimately designed depending on the balloon length.

In accordance with various aspects of the disclosure, the multi-lumen tube 10 may have a Shore hardness of at least 60D and the extension tube 28 may have a hardness less than that of the multi-lumen tube 10 and being no more than 70D, such as a hardness of no more than 69D, 68D, 67D, 66D, 65D, 64D, 63D, 62D, 61D, or no more than 60D. In some aspects, the multi-lumen tube 10 may have a Shore hardness of at least 65D and the extension tube 28 may have a hardness less than that of the multi-lumen tube 10 and being no more than 68D, 67D, 66D, 65D, 64D, 630, 62D, 61D, or no more than 60D. In some aspects, the multi-lumen tube 10 may have a Shore hardness of at least 72D and the extension tube 28 may have a hardness less than that of the multi-lumen tube 10 and being no more than 68D, 67D, 66D, 65D, 64D, 63D, 62D, 61D, or no more than 60D.

The extension tube 28 may have a length proportioned to a length of a desired balloon. According to various aspects of the disclosure, balloon lengths may range from 15 mm to 200 mm, such as a length ranging from 15 mm to 150 mm, and thus, the corresponding extension tube lengths may range from 15 mm to 200 mm±5 mm, such as a length ranging from 15 mm to 150 mm±5 mm. According to some aspects, the extension tube length may be greater than the balloon length by an amount ranging from 3-5 mm.

In some aspects of the disclosure, the total length of the catheter 2 (including the extension tube 28) can range from 40 cm to 150 cm.

Table 1 provides exemplary lengths for the extension tube 28 based on the length and diameter of the balloon 8.

TABLE 1

Exemplary Extension tube lengths.

| Balloon Diameter (mm) | Balloon Length (mm) | Extension tube length (mm) |
|---|---|---|
| 5, 6, 7 | 15 | 19.1 |
| 9, 10, 12 | 20 | 23.5 |

TABLE 1-continued

Exemplary Extension tube lengths.

| Balloon Diameter (mm) | Balloon Length (mm) | Extension tube length (mm) |
|---|---|---|
| 8 | 20 | 23.7 |
| 3, 4, 5, 6, 7 | 20 | 24.5 |
| 9, 10 | 30 | 32.9 |
| 3, 4, 5, 6, 7 | 30 | 33.7 |
| 8 | 30 | 34.2 |
| 9, 10, 12 | 40 | 44.3 |
| 3, 4, 5, 6, 7 | 40 | 44.6 |
| 8 | 40 | 44.7 |
| 9, 10, 12 | 60 | 63.2 |
| 8 | 60 | 64.0 |
| 3, 4, 5, 6, 7 | 60 | 64.5 |
| 3, 4, 5, 6, 7, 8, 9 | 80 | 82.0 |
| 3, 4, 5, 6, 7 | 100 | 102.0 |
| 3, 4, 5, 6, 7 | 120 | 122.0 |
| 3, 4, 5, 6, 7 | 150 | 152.0 |
| 3, 4, 5, 6, 7 | 200 | 202.0 |

Figure 2:
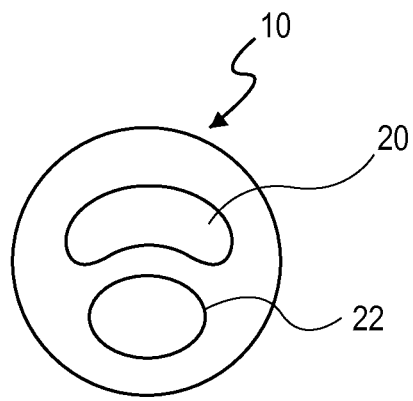
FIG. 2 is a cross-sectional view of the catheter along line II-II of FIG. 1 showing exemplary inflation and guide wire lumens of the multi-lumen tube.

The multi-lumen tube 10 in the examples of Table 1 may comprise 90% 72D Pebax® and 10% nylon 12, whereas the extension tube 28 may comprise 75% 55D Pebae and 25% 72D Pebax®. Nylon 12 is known to increase the stiffness of the shaft. A cross-section of multi-lumen tube 10 is shown in FIG. 2. The multi-lumen tube 10 may have an overall diameter of 0.05 in. and the guide wire lumen 22, being circular, may have a dimension of 0.037 in.±0.002 in. The inflation lumen 20 may have a width of 0.037 in.-±0.002 in. and may be crescent-shaped, having a height of 0.015 in±0.002 in. Different guide wire sizes such as, for example, 0.014 in., 0.018 in., or 0.035 in. may be used.

Figure 4A:
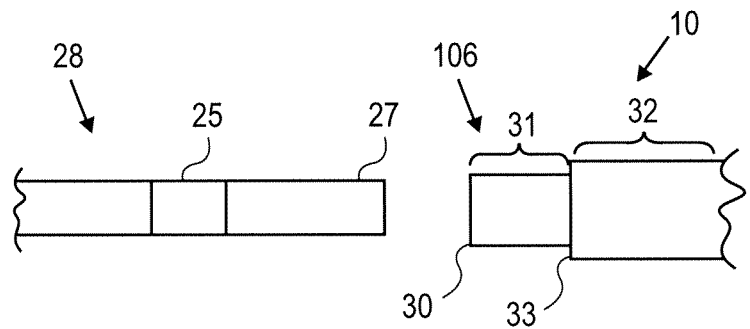
FIGS. 4A-4D are side views of the distal end of the catheter of FIG. 1, without the balloon attached, illustrating a method of making the extended length catheter of FIG. 3.

Referring now to FIGS. 4A-4D, an exemplary method of making an extended length catheter is illustrated and described. According to various aspects of the disclosure, the extension tube 28 may be connected with the multi-lumen tube 10 at the distal end 10b of the multi-lumen tube 10 by, for example, thermally bonding the tubes 10, 28 together. Referring to FIG. 4A, the distal end 10b of the multi-lumen tube 10 may include a reduced diameter portion 31. The reduced diameter portion 31 may be formed, for example, by grinding a portion of the distal end 10b of the multi-lumen tube 10. In some aspects, as a result of the reduction in diameter at the distal end 10b, the inflation lumen 20 may be eliminated from the reduced diameter portion 31. Thus, the reduced diameter portion 31 may be a mono-lumen tube comprising on the guide wire lumen 22. In some aspects, an inflation lumen 120 may be maintained, and the reduced diameter portion may be a multi-lumen tube.

The reduced diameter portion 31 has a length extending from a tip 30 (the most distal tip of the multi-lumen tube 10) to an interface 33, which abuts the remaining portion 32 of the multi-lumen tube 10. The remaining portion 32 remains a dual lumen tube having the inflation lumen 20 and the guide wire lumen 22 and, thus, a diameter greater than that of the reduced diameter portion 31. According to various aspects of the disclosure, the reduced diameter portion 31 may have a length of about 2.5 mm, although other lengths can be used depending on the ultimate length of the catheter 2 and the extension tube 28. In some aspects, the tip 30 of the reduced diameter portion 31 may be flared to expand the opening to the guide wire lumen 22 at the distal tip 30 of the multi-lumen tube 10. The opening to the guide wire lumen 22 may be flared so that the extension tube 28 can be inserted therein without comprising the diameter of the guide wire lumens 22, 29 with regard to slidably receiving the guide wire 12. The flaring can be accomplished by, for example, a flaring tool such as, for example, a mandrel.

The extension tube 28 may comprise a mono lumen and may be cut to a desired length, depending on the diameter and length of the balloon 8. The extension tube 28 may include a marker band 25 over a portion of its outer diameter (but not at the tip of the extension tube 28). The marker band 25 may comprise an annular metal strip, such as, for example, gold, platinum/iridium, or the like, that fits over a catheter. During use of the catheter 2, the position of the marker bands may indicate the ends of the balloon portion when dilated.

Figure 4B:
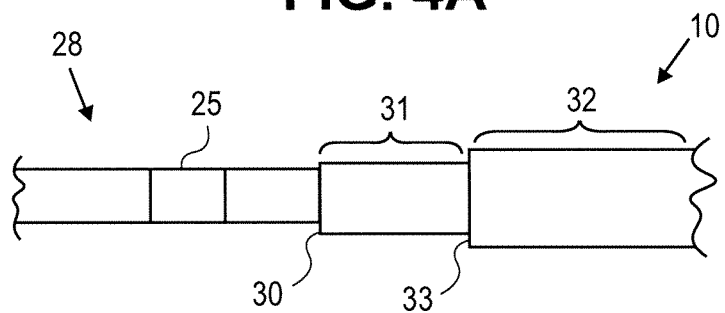

Referring now to FIG. 4B, an end 27 of the extension tube 28 may be inserted into the flared tip 30 of the reduced diameter portion 31 of the multi-lumen tube 10 up to the interface 33 of the remaining portion 32 of the multi-lumen tube 10. The insertion can be performed, for example, with the aid of a mandrel.

Figure 4C:
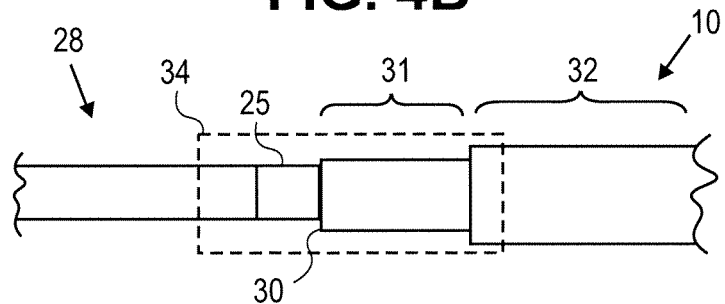

As shown in FIG. 4C, the marker band 25 may be moved, for example, by sliding, relative to the extension tube 28 until it contacts the tip 30 of the reduced diameter portion 31 of the multi-lumen tube 10. The overlap between the extension tube 28 and the multi-lumen tube 10 can range from 0.075 in. to 0.085 in., although other lengths may be appropriate depending on the overall lengths of the catheter 2 and the extension tube 28. According to various aspects of the disclosure, the joined lumens 10, 28 can be held in place, for example, via a heat shrink fitting 34. For example, the fitting 34 may be slid over the end of the extension tube 28, the marker band 25, the reduced diameter portion 31 of the multi-lumen tube 10, and a portion of the remaining portion 32 of the multi-lumen tube 10. The heat shrink fitting 34 may help prevent the marker band 25 from shifting.

Figure 4D:
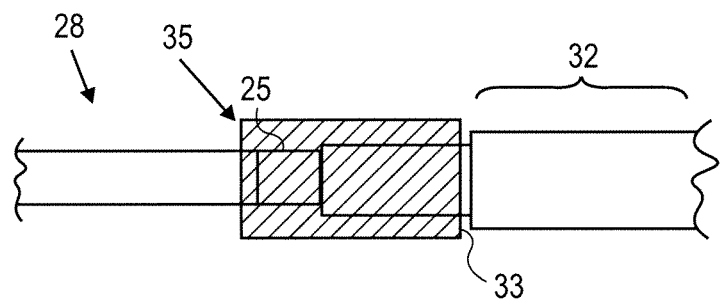

Referring now to FIG. 4D, the jaws 35 of a heat bonder may be fitted over the end of extension tube 28 (including marker band 25) and the reduced diameter portion 31 such that an end of the jaws 35 aligns with the interface 33 of reduced diameter portion 31 and the remaining portion 32.

Upon joining the extension tube 28 to the multi-lumen tube 10, the balloon 8 can be mounted on the distal portion of the catheter 2. In one example, the balloon 8 may be loaded onto the distal end of the tube where the distal end includes the connected extension tube 28. The balloon 8 may include two necks, one at each extremity of the balloon 8, that snugly fit over the distal portion of the catheter 2. For example, the distal neck of the balloon 8 may fit over the extension tube 28 and the proximal neck of the balloon 8 may fit over the multi-lumen tube 10.

It should be appreciated that a heat shrink fitting may be placed, for example, by sliding, over the proximal balloon neck (on the multi-lumen tube 10) and adjacent tube area (i.e., the extension tube 10) and pre-shrunk with a hot air jet to hold the proximal balloon neck in place. Subsequently, the proximal balloon neck may be bonded to the catheter 2 via, for example, a laser, after which the heat shrink fitting can be removed. A second heat shrink fitting may be positioned over the distal balloon neck and the bonding process may be repeated to bond the distal balloon neck to the catheter 2.

In operation, the guide wire 12 may first be directed through a patient's vascular system, for example, by a physician. The catheter 2 may then be advanced over the guide wire 12 via the guide wire lumen 22. Because of the relatively small diameter of the guide wire 12, there may be space within the guide wire lumen 22 to administer fluids to the patient without the need to remove the guide wire 12. The guide wire 12 may further include a smaller diameter main wire that tapers at its distal end. At the distal end, the main wire may be surrounded by a spring to act as a bumper to minimize injury to the vessel wall.

In some aspects, the guide wire 12 may be placed into a coronary artery through the femoral artery and to the site of a stenosis. The distal end 10b of the multi-lumen tube 10 of the catheter 2, including the preloaded balloon 8, may be directed to the site of the stenosis via the guide wire 12. The stenosis may be treated by inflating the balloon 8 with fluid received via the inflation lumen 20 of the multi-lumen tube 10. In some aspects, a stent may be preloaded about the balloon 8 such that inflation of the balloon expands the stent so that the stent may be implanted at the site of the stenosis.

According to various aspects of the disclosure, the aforementioned operation may be used to treat a disease or condition associated with a stenosis or thrombosis of vessels relatively longer than a typical stenosis or thrombosis.

It will be apparent to those skilled in the art that various modifications and variations can be made in the devices and methods of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A balloon catheter comprising:
a multi-lumen tube defining an inflation lumen and a guide wire lumen, the guide wire lumen and the inflation lumen being co-terminus, the multi-lumen tube having a proximal end and a distal end, the distal end defining a flared portion terminating at a distal most flared tip;
an extension tube received within the distal most flared tip and secured to the distal end of the multi-lumen tube at a proximal region of the extension tube; and
a dilatation balloon disposed about the multi-lumen tube and the extension tube, the distal end of the multi-lumen tube being under the balloon.

2. The balloon catheter of claim 1, wherein the balloon has a proximal neck and a distal neck at opposed ends thereof, the proximal neck being at the distal end of the multi-lumen tube and the distal neck being at the extension tube.

3. The balloon catheter of claim 1, wherein the multi-lumen tube and the extension tube comprise different materials.

4. The balloon catheter of claim 3, wherein the multi-lumen tube and the extension tube comprise materials having different Shore hardness values.

5. The balloon catheter of claim 4, wherein the multi-lumen tube has a greater Shore hardness than that of the extension tube.

6. The balloon catheter of claim 5, wherein the multi-lumen tube has a Shore hardness of at least 60D and the extension tube has a hardness less than that of the multi-lumen and being no more than 70D.

7. The balloon catheter of claim 5, wherein the multi-lumen tube has a Shore hardness of at least 65D and the extension tube has a hardness less than that of the multi-lumen and being no more than 65D.

8. The balloon catheter of claim 3, wherein at least one of the multi-lumen tube and the extension tube comprises a nylon material.

9. The balloon catheter of claim 3, wherein at least one of the multi-lumen tube and the extension tube comprises a polyether block polyamide.

10. The balloon catheter of claim 1, wherein the length of the extension tube is greater than the length of the balloon by an amount ranging from 3-5 mm.

11. The balloon catheter of claim 1, wherein the extension tube comprises a monolumen tube configured to receive a guide wire.

12. The balloon catheter of claim 1, wherein the extension tube is received within the guide wire lumen of the multi-lumen tube.

13. The balloon catheter of claim 1, wherein the multi-lumen tube has a first diameter proximally of the distal end of the multi-lumen tube, the distal end of the multi-lumen tube having a second diameter less than the first diameter.

14. The balloon catheter of claim 13, wherein the extension tube is received within an enlarged opening defined by the flared distal tip and leading to the guide wire lumen of the multi-lumen tube.

15. The balloon catheter of claim 1, wherein the multi-lumen tube and the extension tube are independently formed.

16. A balloon catheter comprising:
a multi-lumen tube defining a guide wire lumen and an inflation lumen, and having proximal and distal ends, the distal end having a distal tip defining a flared opening of the guide wire lumen, the guide wire lumen and the inflation lumen having a distal end that is co-terminus with the distal end of the multi-lumen tube;
an extension tube inserted within the flared opening of the guide wire lumen and coupled to the multi-lumen tube and extending distally from the distal end of the multi-lumen tube; and
a dilatation balloon disposed about the multi-lumen tube and the extension tube, the distal end of the multi-lumen tube being under the balloon.

17. The balloon catheter of claim 16, wherein the multi-lumen tube and the extension tube are independently formed.

18. The balloon catheter of claim 16, wherein the proximal end of the multi-lumen tube defines a first diameter, the distal end of the multi-lumen tube having a reduced diameter portion extending to the distal tip and defining a second diameter less than the first diameter.

19. The balloon catheter of claim 18, wherein the reduced diameter portion of the multi-lumen tube includes the guide wire lumen and the inflation lumen.

20. The balloon catheter of claim 18, wherein the reduced diameter portion of the multi-lumen tube includes the guide wire lumen and is devoid of the inflation lumen.

21. A balloon catheter comprising:
a catheter having proximal and distal ends, the catheter defining a guide wire lumen and an inflation lumen and having a reduced diameter portion adjacent the distal end, the reduced diameter portion leading to a distal most tip and having a flared opening communicating with the guide wire lumen;
an extension tube positioned within the flared opening and coupled to the catheter, the extension tube extending distally from the catheter, the extension tube includes a guide wire lumen in communication with the guide wire lumen of the catheter and an inflation lumen in communication with the inflation lumen of the catheter; and
a dilatation balloon in fluid communication with the inflation lumen, the dilatation balloon having a proximal neck secured to distal end of the catheter and a distal neck secured to the extension tube.

22. The balloon catheter of claim 21, wherein the catheter is a single tube.

23. The balloon catheter of claim 21, wherein the extension tube is a mono lumen tube defining a guide wire lumen in communication with the guide wire lumen of the catheter.

24. The balloon catheter of claim 21, wherein the multi-lumen tube and the extension tube are independently formed.

\* \* \* \* \*